US008621943B2

(12) United States Patent
Swanda

(10) Patent No.: US 8,621,943 B2
(45) Date of Patent: Jan. 7, 2014

(54) METHOD OF SINGULATING EMBRYOS

(75) Inventor: Anthony P. Swanda, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 514 days.

(21) Appl. No.: 12/870,065

(22) Filed: Aug. 27, 2010

(65) Prior Publication Data

US 2011/0076715 A1   Mar. 31, 2011

Related U.S. Application Data

(60) Provisional application No. 61/247,047, filed on Sep. 30, 2009.

(51) Int. Cl.
*G01N 1/00* (2006.01)

(52) U.S. Cl.
USPC ............................................. 73/863; 222/52

(58) Field of Classification Search
None
See application file for complete search history.

(56) References Cited

U.S. PATENT DOCUMENTS

| 5,284,765 | A | 2/1994 | Bryan et al. | |
|---|---|---|---|---|
| 5,701,699 | A | 12/1997 | Carlson et al. | |
| 6,684,564 | B1 * | 2/2004 | Hirahara | 47/57.6 |
| 7,685,767 | B2 * | 3/2010 | Timmis et al. | 47/57.6 |
| 8,323,177 | B2 * | 12/2012 | Wong et al. | 600/34 |
| 8,337,387 | B2 * | 12/2012 | Wong et al. | 600/33 |
| 2001/0036668 | A1 | 11/2001 | Furlong et al. | |
| 2004/0267457 | A1 | 12/2004 | Timmis et al. | |
| 2005/0114918 | A1 | 5/2005 | Hirahara et al. | |
| 2009/0142837 | A1 * | 6/2009 | Adams et al. | 435/441 |
| 2011/0153093 | A1 * | 6/2011 | Aidun | 700/282 |

FOREIGN PATENT DOCUMENTS

WO   0113702 A2   3/2001

OTHER PUBLICATIONS

Harrell, et al., Automated, in vitro harvest of somatic embryos, Agricultural Engineering and Horticultural Science, University of Florida, Gainesville, FL 32611 USA, Plant Cell Tissue and Organ Culture 39: 171-183, 1994.

Ibaraki, Y et al., "Automation of somatic embryo production", 2001, vol. 65, pp. 179-199, Plant Cell, Tissue and Organ Culture, p. 192, col. 2, line 39-line 49.

Gupta, PK et al., "Masspropagation of conifer trees in liquid cultures-progress towards commercialization", 2005, vol. 81 pp. 339-346, Plant Cell, Tissue and Organ Culture, p. 344, col. 1, line 39-col. 2, line 13 and the whole document.

* cited by examiner

*Primary Examiner* — Robert R Raevis
(74) *Attorney, Agent, or Firm* — Christensen O'Connor Johnson Kindness LLP

(57) ABSTRACT

A method of singulating embryos is provided. The method includes providing a plurality of embryos (40) within a system (20) and sensing (34) at least one of the plurality of embryos in a fluid. The method also includes dispensing (26) at least one of the plurality of embryos on a surface (28).

8 Claims, 5 Drawing Sheets

METHOD OF SINGULATING EMBRYOS

CROSS-REFERENCE TO RELATED APPLICATION

This application is entitled to and claims the benefit of priority under 35 U.S.C. §119 from U.S. Provisional Patent Application Ser. No. 61/247,047 filed Sep. 30, 2009, and titled "Method of Singulating Embryos," the contents of which are incorporated herein by reference.

BACKGROUND

A sexual propagation for plants has been shown for some species to yield large numbers of genetically identical embryos, each having the capacity to develop into a normal plant. Such embryos must usually be further cultured under laboratory conditions until they reach an autotrophic "seedling" state characterized by an ability to produce their own food via photosynthesis, resist desiccation, produce roots able to penetrate soil, and fend off soil microorganisms. Some researchers have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed shell, synthetic gametophyte and a plant embryo. A manufactured seed that does not include the plant embryo is known in the art as a "seed blank." Such a seed blank typically is a cylindrical capsule having a closed end and an open end. Synthetic gametophyte is placed within the seed shell to substantially fill the interior of the seed shell. A longitudinally extending hard porous insert, commonly known as a cotyledon restraint, may be centrally located within the synthetic gametophyte and includes a centrally located cavity extending partially through the length of the cotyledon restraint. The cavity is sized to receive the plant embryo therein. The well-known plant embryo includes a radicle end and a cotyledon end. The plant embryo is deposited within the cavity of the cotyledon restraint cotyledon end first and is sealed within the seed blank by at least one end seal. There is a weakened spot in the end seal to allow the radicle end of the embryo to penetrate the end seal.

There are automated processes available to mass produce manufactured seeds of the type described above. One such automated process is described in U.S. patent application Ser. No. 10/982,951, entitled System and Method of Embryo Delivery for Manufactured Seeds, and assigned to Weyerhaeuser Company of Federal Way, Washington, the disclosure of which is hereby expressly incorporated by reference.

Currently, embryos are manually plucked from a growing medium and are physically placed on the plate for retrieval and insertion into a seed blank. Although such manual processes are effective, they are not without their limitations. As a non-limiting example, such manual operations are both labor and time intensive and, therefore, expensive. As part of the process to produce large numbers of somatic embryos available for insertion in manufactured seeds, it is desirable to minimize the manual labor element from the process.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method of singulating embryos is provided. The method includes providing a plurality of embryos within a system and sensing at least one of the plurality of embryos in a fluid. The method also includes dispensing at least one of the plurality of embryos on a surface.

DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION

Figure 1:
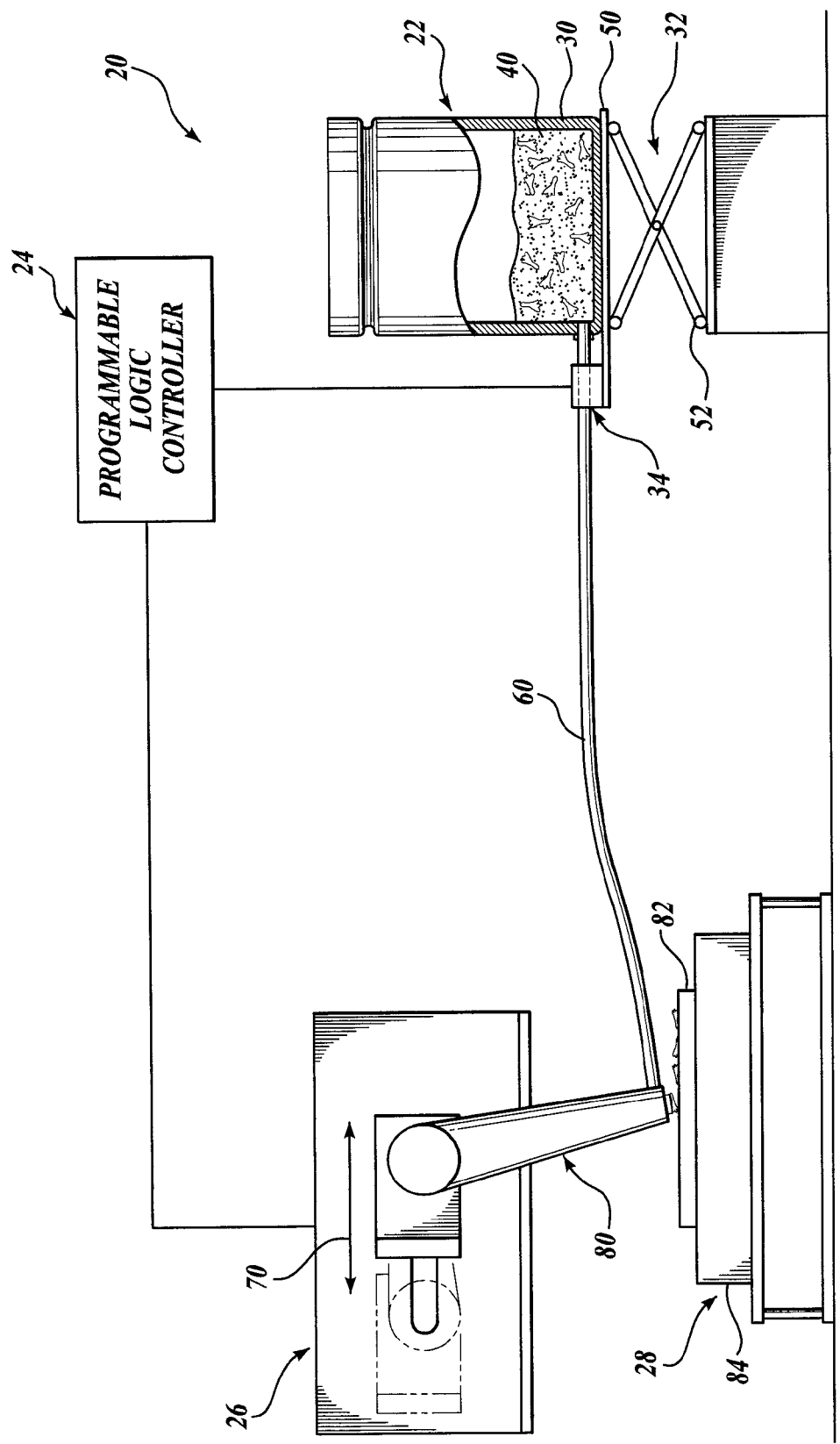
FIG. 1 is a diagrammatical view of one example of a system using a method of singulating embryos in accordance with one embodiment of the present disclosure.

FIG. 1 diagrammatically depicts an automated system 20 for implementing a method of singulating embryos in accordance with one embodiment of the present disclosure. The system 20 is suitably mounted in conjunction with an assembly for assembling manufactured seeds (not shown) or is remotely located from such an assembly.

The system 20 includes an embryo storage assembly 22, a programmable logic controller (PLC) 24, a placement mechanism 26, and an embryo deposit assembly 28. The embryo storage assembly 22 includes a singulation vessel 30, a lift mechanism 32, and a sensor 34. The singulation vessel 30 is suitably a container having a plurality of embryos 40 suspended in a fluid, such as a sterile, Nanopure water. Preferably, the fluid is agitated to a sufficient degree to suspend all embryos 40. The singulation vessel 30 is mounted on the lift mechanism 32.

The lift mechanism 32 includes a base plate 50 coupled to a well-known lift 52, such as a screw drive or a scissor lift, to assist in maintaining a substantially constant head at the outlet of the singulation vessel 30. Within the meaning of this disclosure and used in this context, the term "substantially" is intended to include engineering acceptable variations resulting in a nearly constant fluid flow rate.

Although the use of a lift 52 to assist in maintaining a substantially constant head, other devices known to maintain a substantially head are also acceptable. As a non-limiting example, a pump (not shown) may be placed in fluid communication with the singulation vessel 30 to maintain the substantially constant flow rate. Thus, such devices are acceptable equivalents and are within the scope of the present disclosure. Further, while maintaining a substantially constant head is preferred, a variable head is also within the scope of the present disclosure as described in greater detail below.

Embryos 40 are transported between the singulation vessel 30 and the placement mechanism 26 by fluid flowing through tubing 60. The tubing 60 extends between the singulation vessel 30 and the placement mechanism 26 and the sensor 34 is suitably positioned adjacent the tubing 60 to sense and/or detect embryos 40 within the tubing 60, as described in greater detail below.

In the illustrated and exemplary embodiment, the flow rate of embryos 40 through the tubing 60 is controlled by the lift 52. Specifically, and as is well-known, the flow rate within the tubing 60 is proportional to the square root of the vertical distance between the outlet of the tubing 60 at the placement mechanism 26 and the liquid level in the singulation vessel 30. As the fluid in the singulation vessel 30 is decreased, the height of the singulation vessel 30 is raised by the lift mechanism 32. The lift 52 raises the singulation vessel 30 at a fixed rate proportional to the flow rate of fluid inside of the tubing 60 to maintain a substantially constant flow rate. In other embodiments, the lift 52 may be raised or lower to increase or decrease, respectively, the flow rate.

The tubing 60 includes an inner diameter sufficiently large to permit entry of a single embryo 40 to enter the tubing 60 at any given time. Although multiple embryos 40 may be positioned longitudinally within the tubing 60, it is desirable that only a single embryo may enter the tubing 60 at any given time. It is also preferred that the tubing 60 be of a material, such as silicone, that is transparent or semi-transparent to permit detection of an embryo within the tubing 60 by the sensor 34.

The sensor 34 is a well-known, laser-based visual sensor used to detect when an embryo 40 exits the singulation vessel 30. One such sensor 34 is model No. LV-H300/100 Series, manufactured and sold by Keyence Corporation of Osaka, Japan. The sensor 34 is suitably mounted to the base plate 50 with the tubing 60 operatively disposed between components of the sensor 34. The sensor 34, in turn, is in communication with the PLC 24.

The system 20 may include a second, well-known sensor (not shown) in communication with the singulation vessel 30. This second sensor is used to measure the hydrostatic head of the fluid in the singulation vessel 30. One such sensor is model No. FW-H07, manufactured and sold by Keyence Corp. of Osaka, Japan. Such a sensor uses ultrasonic sound waves to measure distance. Although an ultrasonic sensor is preferred, other types of sensors, including laser and radar based, are within the scope of the present disclosure. The second sensor is in communication with the PLC 24.

The well-known PLC 24 suitably has an operator interface to control the singulation process and the raising and lowering of the lift mechanism 32. One such PLC 24 is a DirectLOGIC 205 Modular Programmable Logic Controller (DL205 PLC), manufactured and sold by Koyo Electronics Industries Co., Ltd. of Tokyo, Japan.

The PLC 24 is programmable to interface with the lift mechanism 32, the sensor 34, the second sensor, and the placement mechanism 26 during operation of the system 20, as well as to permit the operator to adjust operational parameters. Operational parameters, such as the number of embryos 40 placed on the embryo deposit assembly 28, the spacing between the embryos 40, and the location of embryos 40 on the embryo deposit assembly 28 may all be programmed as desired.

The PLC 24 may be programmed to control the spacing and placement of embryos 40 on the embryo deposit assembly 28 by tracking the embryo as it flows through the tubing 60. In such an embodiment, the PLC 24 includes a clock or timer and a registry. One such registry is an embryo location registry ("ELR"). The ELR includes binary registers that represent locations along the length of the tubing 60. As an example, the ELR may segregate the tubing 60 into fifty registers, which represent fifty sequential locations in the tubing 60. The first register location is suitably located closest to the sensor 34 and the last register is located at the end of the tubing 60 where it connects to the placement mechanism 26. The ELR tracks and logs as a function of time the path of embryos within the tubing 60, as described in greater detail below.

The placement mechanism 26 includes a robotic arm 80. Motion of the robotic arm 80 is controllable relative to the embryo deposit assembly 28 to position the outlet of the tubing 60 over an open location on the embryo deposit assembly 28. One suitable robotic arm 80 is an Ultramotion robotic arm, model No. DA25-HT17-8 NO-B/4, manufactured and sold by Ultramotion of Mattituck, N.Y. To achieve the desired motion of the robotic arm 80, the placement mechanism 26 also includes a well-known stepping motor (not shown), such as model No. PK266-E2.0A, manufactured and sold by Oriental Motor U.S.A. Corp. of Torrance, Calif.

The robotic arm 80 has two degrees of freedom to provide precise placement of embryos 40 on the embryo deposit assembly 28. In that regard, it is preferred that the robotic arm 80 translates longitudinally along an axis indicated by the arrow 70. Further, the robotic arm 80 moves along the axis perpendicular to arrow 70, i.e., in and out of the page. The outlet of the tubing 60 on the robotic arm 80 is suitably oriented at an angle relative to a vertical axis so that, as the fluid exits from the tubing 60, it is not perpendicular to the embryo deposit assembly 28.

It is also desirable that the robotic arm 80 is controlled by the PLC 24, in combination with the ELR, sensor 34, and/or the second sensor. As a non-limiting example, if an embryo 40 is detected by the sensor 34, it sends a signal to the PLC 24 indicating the presence of the embryo. This signal is entered in the ELR as a "true." If an embryo 40 is not detected by the sensor 34, then the register is "false." A "true" registry is noted as a "1," while a "false" registry is noted as a "0."

The number of registries in the ELR is a function of the length of the tubing 60. For example, if the tubing 60 is 20 inches long and there are fifty registers, each register represents 0.4 inches of tubing 60. Further, in this example, the travel time of an embryo from the sensor 34 to the placement mechanism 26 is approximately one second. As a result, each registry of the ELR represents approximately 20 ms of time. The clock updates the registry every 20 ms, such that the registers are shifted forward and each register is updated with a "1" or a "0." Further, the speed of the robotic arm 80 is also updated every 20 ms and is programmed to match the spacing between the embryos, as desired by the operator to control the spacing of the embryos deposited onto the embryo deposit assembly 28.

The embryo deposit assembly 28 includes a singulation frame 82 and a drainage vessel 84. The singulation frame 82 suitably includes a supporting material that allows fluid to pass through while retaining embryos. The supporting material also preferably provides a color contrast between the supporting material and the embryo such that there is contrast between the embryos and the supporting material. One such supporting material suitable for use with the system 20 is Nitex® nylon, model No. 03-125/45. The drainage vessel 84 suitably supports a vacuum (not shown) for fluid removal and to aid in holding the embryos in a fixed location.

Figure 2A:
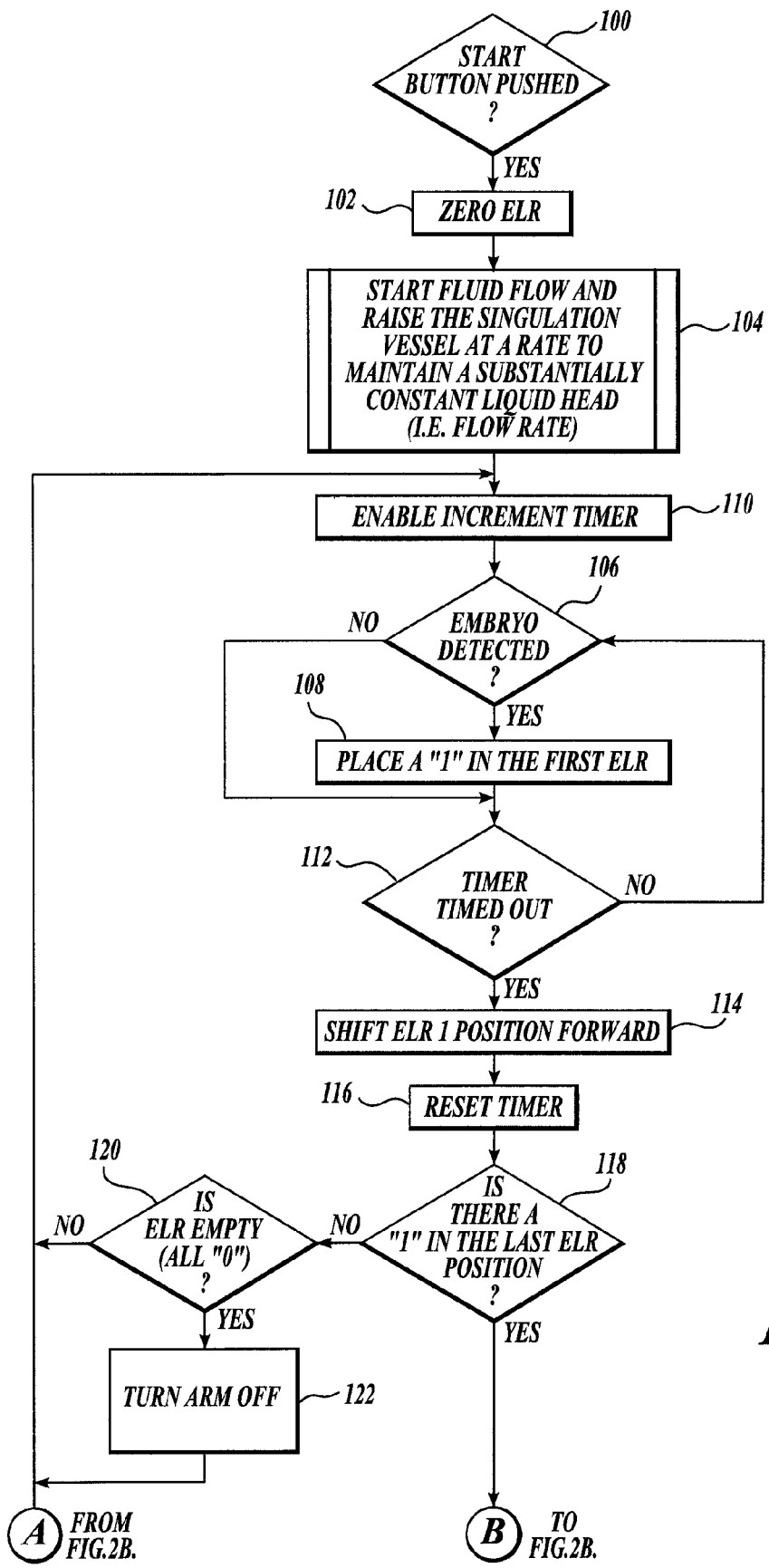
FIG. 2A is a flow diagram of a method of singulating embryos in accordance with one embodiment of the present disclosure.
Figure 2B:
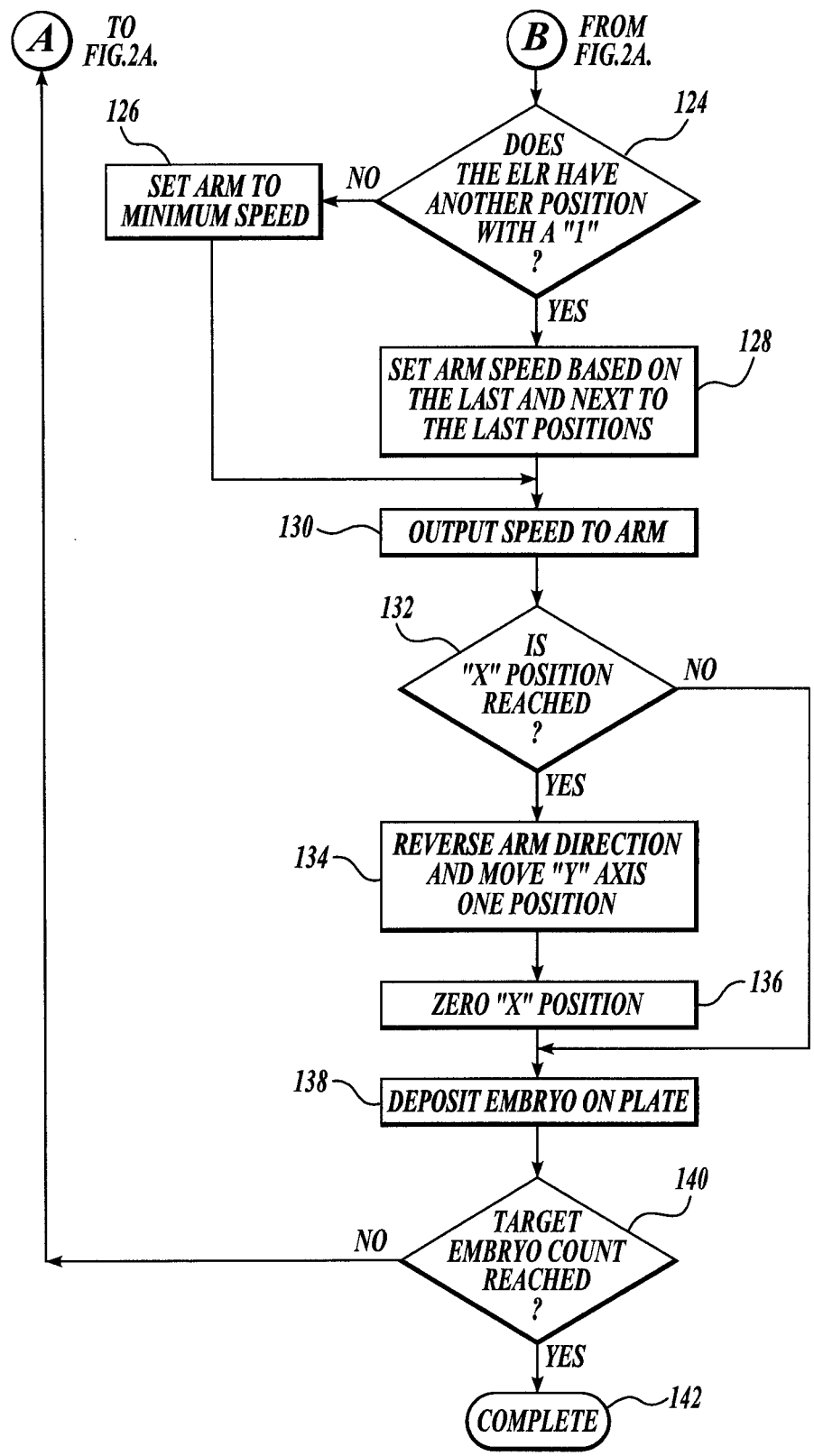
FIG. 2B is a continuation of the flow diagram of FIG. 2A.

Operational aspects of the system 20 constructed in accordance with one embodiment of the present disclosure may be best understood by referring to FIGS. 2A-2B. The beginning of the operational sequence is represented by the start block 100 by initiating the system 20 to zero the ELR, indicated by the block 102. Also, fluid flow through the system 20 is initiated and the lift mechanism 32 raises the singulation vessel 30 at a rate to maintain a substantially constant liquid head throughout the system 20. This is illustrated by the block 104.

The timer is enabled, indicated by block 110, and the sensor 34 determines whether an embryo 40 is detected in the tubing 60 and indicated by the decision block 106. If an embryo 40 is detected by the sensor 34, a "1" is placed in the first registry location of the ELR, indicated by the block 108. Thereafter, the timer is evaluated to determine whether or not a predetermined period of time, such as 20 ms, has expired, and as indicated by the decision block 112. If an embryo is not detected by the sensor 34, the PLC will advance ahead to the block 112 and evaluate whether the timer has timed out.

If the timer has not timed out, the ELR returns to block 106 to evaluate whether an embryo has been detected. If the timer has timed out, then the ELR shifts the registry by one position forward, indicated by the block 114. Also, as indicated by the block 116, the timer is reset.

As indicated by the block 118, the PLC evaluates whether there is a "1" in the last ELR registry, indicating the presence of an embryo 40 at the very end of the tube 60. If there is a "0" in the last registry, indicating that there is no embryo in the last registry, the PLC determines whether every registry of the ELR is a "0," indicated by the block 120. If every registry is empty, the robotic arm 80 is turned off, as indicated by the block 122, and the PLC returns back to block 110 to enable the increment timer and to evaluate whether an embryo is again detected by the sensor 34, as indicated by block 106.

Referring back to the block 118, if the last registry in the ELR contains a "1," then the PLC evaluates whether any other registry in the ELR contains a "1," thereby indicating the presence of another embryo in the tubing 60. This is indicated by the block 124. As represented by the block 126, if no other registry in the ELR contains a "1," then the speed of the robotic arm 80 is set to a minimum speed. This may be accomplished by an inclusion of a lookup table containing predetermined robotic arm speeds as a function of the number of embryos in the tubing 60. Such a lookup table is well-known to one of ordinary skill in the art.

If there is a "1" in any one or more other registry of the ELR, then the PLC sets the robotic arm speed based on the last and next to the last registry positions in the ELR by referring to the lookup table, as noted above. This is indicated by the block 128. Thereafter, as indicated by the block 130, the output speed is transmitted to the robotic arm 80.

Before depositing the embryo onto the singulation frame 82, the "X" position of the robotic arm 80 relative to the width of the singulation frame 82 is evaluated. Specifically, as indicated by the block 132, the "X" position of the robotic arm 80 is evaluated to determine whether it has reached the maximum width of the singulation frame 82. If yes, then the robotic arm 80 is advanced one position forward in the longitudinal direction, or "Y" direction, of the singulation frame 82 and the direction of the robotic arm 80 in the "X" direction is reversed, as indicated by the block 134.

After the "X" position of the robotic arm 80 is reversed, the PLC zeroes out the "X" position, indicated by the block 136. Thereafter, the embryo is deposited on the singulation frame 82, as indicated by the block 138. Returning to block 132, if the "X" position is not reached, the blocks 134 and 136 are bypassed and the embryo is deposited on the singulation frame 82, as noted in block 138.

It is desired that the PLC 24 be programmed to control the robotic arm 80 such that it deposits embryos in a predetermined position on the singulation frame 82. As a non-limiting example, the PLC 24 may be programmed such that the robotic arm 80 deposits embryos on the singulation frame 82 on their sides. In such a position, both the cotyledon and radical ends contact the supporting material of the singulation frame 82, or only the cotyledon or radical end contacts the supporting material of the singulation frame 82. As another non-limiting example, the robotic arm 82 may deposit embryos on the supporting material such that succeeding embryos are spaced from preceding embryos. Accordingly, such predetermined positions, as well as equivalents thereof, are within the scope of the disclosure.

After the embryo is deposited on the singulation frame 82, and as indicated by the block 140, the ELR determines whether a desired number of embryos deposited on the singulation frame 82 have been reached. If "no," the ELR is returned to block 110 and the evaluation is repeated. If the maximum number of embryos has been deposited on the singulation frame 82, the process is now complete, as indicated by the block 142.

Figure 3A:
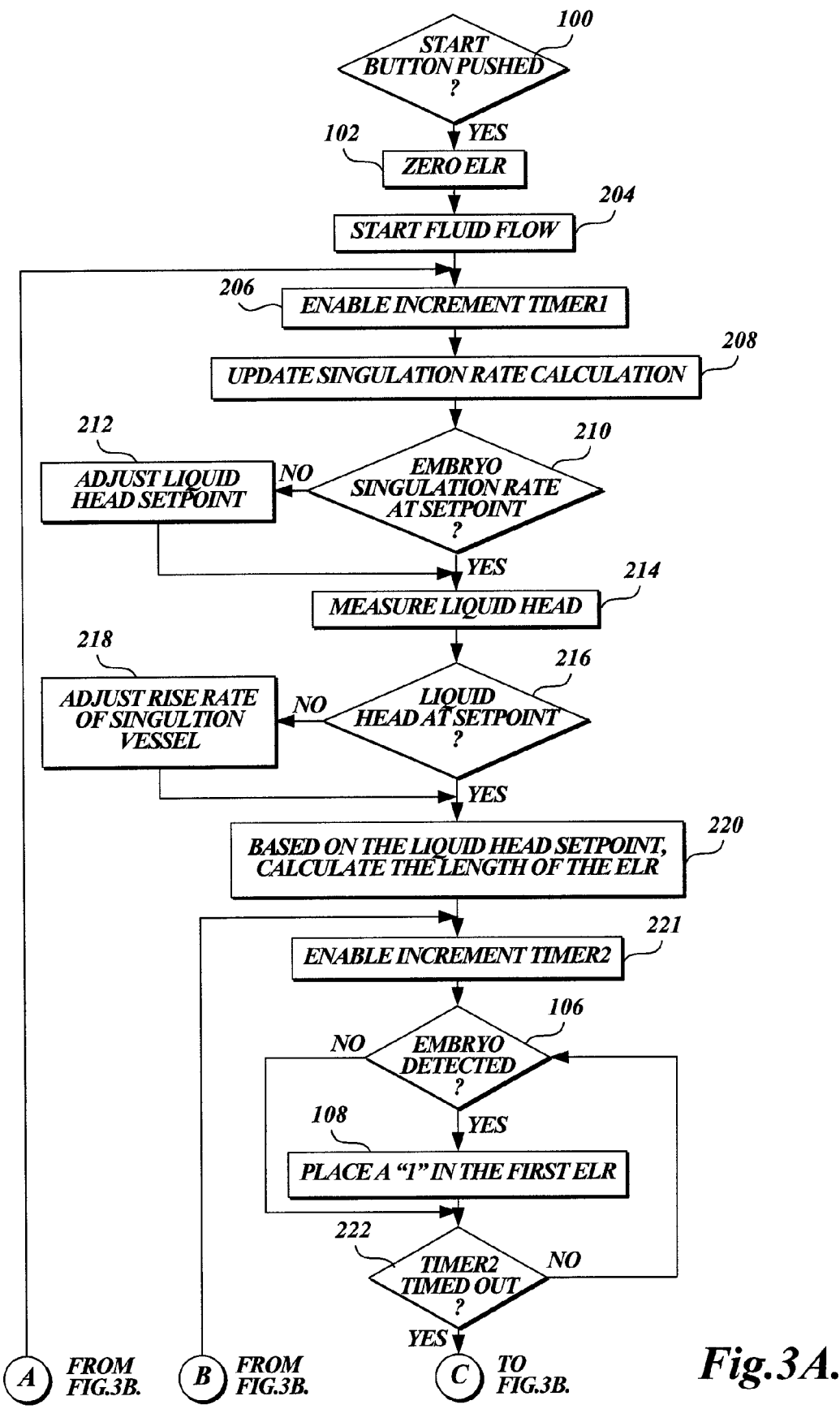
FIG. 3A is a flow diagram of a method of singulating embryos in accordance with another embodiment of the present disclosure.
Figure 3B:
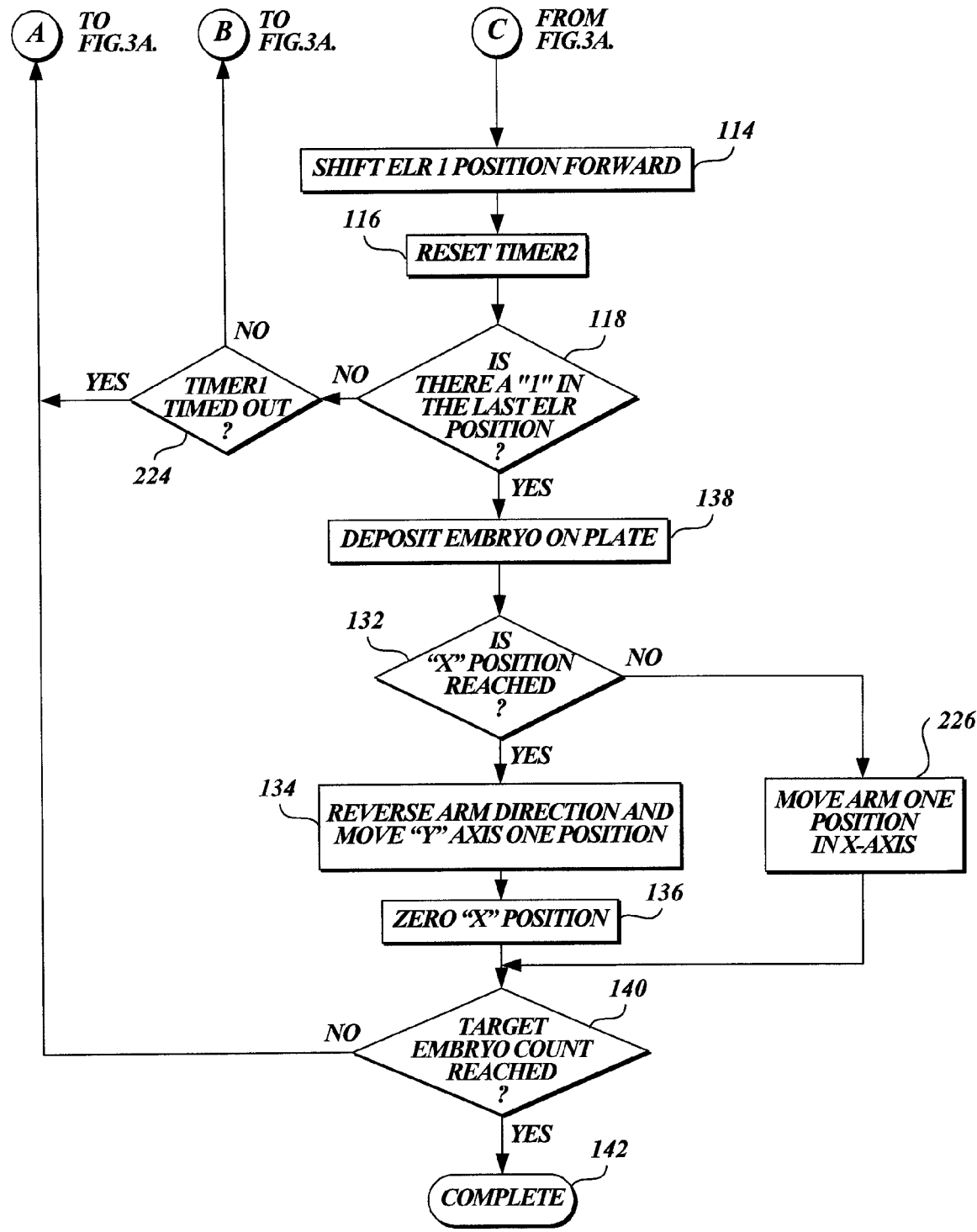
FIG. 3B is a continuation of the flow diagram of FIG. 3A.

Operation of an alternate method of singulating embryos may be best understood by referring to FIGS. 3A and 3B. It should be noted that components of this alternate embodiment that are the same as those described with respect to the first embodiment of FIGS. 3A and 3B have the same reference number.

The beginning of the operational sequence is represented by the start block 100 by initiating the system 20 to "0" the ELR, indicated by the block 102. Simultaneously, fluid flow through the system 20 is initiated and indicated by the block 204. An increment timer 1 is enabled, indicated by the block 206, and the singulation rate, or data point, is calculated, as indicated in the block 208.

The embryo singulation rate is compared to the set point to determine whether or not the embryo singulation rate is equal to the set point, as indicated by the decision block 210. The singulation rate is defined as the number of detected embryos per unit time. To calculate it, the number of embryos detected in a moving window of time is divided by the size (in time) of the window, e.g., 50 detections in the last 60 seconds. The window is "moving" forward in time, as the most recent window is always used. If the embryo singulation rate does not equal that set point, the hydrostatic head setpoint is adjusted. If the singulation rate needs to be decreased, the hydrostatic head setpoint is lowered. This is indicated by the block 212. Then the hydrostatic head of the liquid within the singulation vessel 30 is measured by the second sensor. One such ultrasonic sensor is described above. This is indicated by the block 214.

Still referring to FIG. 3A, a comparison of the liquid hydrostatic head is made relative to the set point to determine whether or not the hydrostatic head is equal to the set point, as indicated by the block 216. If the hydrostatic head is not at the set point, the raise rate of the singulation vessel 30 by the lift mechanism 32 is adjusted, as indicated by the block 218. In summary, the singulation rate controller adjusts the hydrostatic head setpoint (i.e., the target flow rate of fluid/embryos) and the hydrostatic head controller adjusts the rise rate of the singulation kettle in an attempt to drive the hydrostatic head to its target (aka setpoint). Following adjustment of the hydrostatic head, calculate the length (i.e., number of registers) of the ELR, as indicated by the block 220. The length of the ELR is calculated based on the distance between the sensor (34) and the outlet of tubing (60) and the flow rate of the fluid (i.e., hydrostatic head). As the flow rate (head) increases the velocity of the fluid/embryos increases in tubing (60), which is turn reduces the time between detection and placement on s-frame (82). The number of registers required is this time divided by the time of timer 2 in block 220. Following block 220, a second increment timer is enabled, as shown in the block 221.

The sensor 34 determines whether an embryo 40 is detected in the tubing 60 and indicated by the decision block 106. If an embryo 40 is detected by the sensor 34, a "1" is placed in the first registry location of the ELR, indicated by the block 108. Thereafter, the second increment timer is evaluated to determine whether or not a predetermined period of time, such as 20 milliseconds, has expired, and as indicated by the decision block 222. If an embryo is not detected by the sensor 34, the PLC will advance ahead to block 222 to determine whether the second increment timer has timed out.

If the second increment timer has not timed out, the ELR returns to block 106 to evaluate whether an embryo has been detected. If the second increment timer has timed out, then the ELR shifts the registry by one position forward and places a "1" in the next registry location, indicated by the block 114. Also, as indicated by the block 116, the second increment timer is reset.

As indicated by the decision block 118, the PLC evaluates whether there is a "1" in the last or "trigger" ELR registry, indicating the presence of an embryo 40 at the very end of the tube 60. If there is a "0" in the last registry, indicating that there is no embryo in the last or trigger registry, the PLC determines whether the first incremental timer has timed out, indicated by the decision block 224. If the first incremental timer has not timed out, then the PLC will advance back to enable the second increment timer, indicated by the block 221. If, however, the first increment timer has timed out, the PLC returns back to enable Timer1, as indicated by the block 206.

Returning to the decision block 118, if the last or trigger registry in the ELR contains a "1," then the PLC deposits an embryo on the singulation frame 82, as noted in the block 138. After depositing the embryo onto the singulation frame 82, the "X" position of the robotic arm relative to the width of the singulation frame 82 is evaluated. Specifically, as indicated by the block 132, the "X" position of the robotic arm 80 is evaluated to determine whether it has reached the maximum width of the singulation frame 82. If it has reached the maximum width of the singulation frame 82, then the robotic arm 80 is advanced one position forward in the longitudinal direction, or "Y" direction, of the singulation frame 82, and the direction of the robotic arm 80 in the "X" direction is reversed, as indicated by the block 134. After the "X" position of the robotic arm is reversed, the PLC zeroes out the "X" position, indicated by the block 136.

If the "X" position is not reached in block 132, the robotic arm 80 is moved one position in the "X" axis, as indicated by the block 226. Doing so moves the robotic arm 80 to the next open position on the singulation frame 82. Thus, removal of at least one of the plurality of embryos may be synchronized with the data point, such as the hydrostatic head, and the flow rate.

Thereafter, the PLC determines whether a desired number of embryos deposited on the singulation frame 82 have been reached, as indicated by the block 140. If the desired number of embryo counts has not been reached, the program returns to block 204 and the process is repeated. If the maximum number of embryos has been deposited on the singulation frame 82, the process is now complete, as indicated by the block 142.

While illustrative embodiments have been illustrated and described, it will be appreciated that various changes can be made therein without departing from the spirit and scope of the invention. As a non-limiting example, the sensor 34 may be positioned at any point along the tubing 60. In one alternate embodiment, the sensor 34 may be positioned adjacent the robotic arm 80. In such an alternate embodiment, the PLC 24 may be programmed to actuate the robotic arm 80 to deposit the sensed embryo as soon as it receives an input signal from the sensor 34. Positioning the sensor 34 adjacent the robotic arm 80 works in a system 20 that has either constant or non-constant fluid flow. Also, the method of the present disclosure may be implemented in a variety of systems and, therefore, the described system for implementing the method is provided for illustration purposes only and is not intended to be limiting.

The embodiments of the invention in which an exclusive property or privilege is claimed are defined as follows:

1. A method of singulating embryos, comprising:
    (a) providing a plurality of embryos in a fluid;
    (b) sensing at least one of the plurality of embryos by a sensor;
    (c) maintaining a substantially constant flow rate of embryos in a tube past the sensor;
    (d) tracking the at least one of the plurality of embryos within the tube; and
    (e) depositing the at least one of the plurality of embryos on a surface.

2. The method of claim 1, wherein the at least one of the plurality of embryos is deposited at a predetermined position on the surface.

3. The method of claim 2, wherein the predetermined position includes lying the at least one of the plurality of embryos on its side.

4. The method of claim 2, wherein the predetermined position includes spacing the at least one of the plurality of embryos from a second embryo positioned on the surface.

5. The method of claim 1, the sensor is in communication with a central processing unit to control depositing the at least one of the plurality of embryos on a surface.

6. The method of claim 5, wherein depositing the at least one of the plurality of embryos on a surface includes a robotic arm in communication with the central processing unit.

7. The method of claim 6, wherein the central processing unit is programmable to control motion of the robotic arm.

8. The method of claim 7, wherein motion of the robotic arm is programmed as a function of the substantially constant fluid flow rate.

* * * * *